United States Patent [19]
Singh et al.

[11] Patent Number: 5,847,102
[45] Date of Patent: Dec. 8, 1998

[54] COLD INDUCED PROMOTER FROM WINTER *BRASSICA NAPUS*

[75] Inventors: Jas Singh, Nepean; Theresa Catherine White; Chao Jiang, both of Ottawa, all of Canada

[73] Assignees: Her Majesty the Queen in right of Canada as represented by the Minister of Agriculture; Agri-Food Canada, both of Ottawa, Canada

[21] Appl. No.: 421,044

[22] Filed: Apr. 12, 1995

[30] Foreign Application Priority Data

Apr. 10, 1995 [CA] Canada ................................... 2146712

[51] Int. Cl.$^6$ .......................... C12N 15/29; C12N 15/82; C12N 15/11; A01H 1/00
[52] U.S. Cl. .................... 536/24.1; 536/23.6; 435/172.3; 435/320.1; 800/205; 800/DIG. 17
[58] Field of Search .................................. 536/23.6, 24.1; 800/205, DIG. 17; 435/172.3, 320.1

[56] References Cited

FOREIGN PATENT DOCUMENTS

| 2099917 | 8/1990 | Canada | C12N 15/72 |
|---|---|---|---|
| 2044606 | 5/1991 | Canada | C12N 015/29 |
| WO 92/19718 | 11/1992 | WIPO | C12N 1/15 |

OTHER PUBLICATIONS

White et al, Regulation of BN115, a Low–Temperature–Responsive Gene from Winter *Brassica napus*. Plant Physiol., vol. 106 (1994) pp. 917–928.

Singh et al, Biochemical and Cellular Mehcanisms of Stress Tolerance in Plants, NATO ASI Series, vol. H 86, Biochemical and Cellular Mechanisms of Stress Tolerance in Plants (1994) pp. 557–567.

Weretilnyk et al Characterization of Three Related Low–Temperature–Regulated cDNAs from Winter *Brassica napus*, Plant Physiol., vol. 101 (1993) pp. 171–177.

Baker et al, The 5'–region of *Arabidopsis thaliana* cor15a has cis–acting elements that confer cold–, drought–and ABA–regulated gene expression. Plant Molecular Biology, vol. 24, (1994) pp. 701–713.

Yamaguchi–Shinozaki et al, A novel cis–acting element in an arabidopsis gene is involved in responsiveness to drought, low–temperature, or high–salt stress. The Plant Cell, vol. 6 (1994), pp. 251–264.

Orr et al, Complementary DNA sequence of a low temperature–induced *Brassica napus* gene with homology to the *Arabidopsis thaliana* kin1 gene. Plant Physiol., vol. 98 (1992), pp. 1532–1534.

Plant Physiol, vol. 99, No. 1 (Suppl.), p. 78 (Abstract No. 467). (1992) White, TC, Simmonds, D, Singh, J. Annual Meeting of the American Society of Plant Physiologists, Pittsburg, Pennsylvania, USA, Aug. 1–5.

*Primary Examiner*—David T. Fox
*Assistant Examiner*—Thomas Haas
*Attorney, Agent, or Firm*—Heslin & Rothenberg, P.C.

[57] ABSTRACT

A 1.2 kb fragment of the 5' regulatory region (from bp –1107 to +100) was fused to the GUS (β-glucuronidase) reporter gene and BN115-promoted GUS expression was observed in green tissues of transgenic *Brassica napus* plants only after incubation at 2° C. No expression was observed after incubation at 22° C., either in the presence or absence of abscisic acid. Microprojectile bombardment of winter *B. napus* leaves with a BN115 promoter/GUS construct yielded similar results and was used to analyze a series of deletions from the 5' end of the promoter. Results obtained from transient expression studies showed that the low temperature regulation of BN115 expression involves a possible enhancer region between bp –1107 and –606 and a second positive regulatory region located between bp –302 and –274. Deletion analyses and results from replacement with a truncated CaMV (cauliflower mosaic virus) 35S promoter suggest that the minimal size required for any maintenance of low temperature GUS expression is a –300 bp fragment. Within this fragment are two 8 bp elements with the sequence TGGCCGAC, which are identical to those present in the positive regulatory region of the promoter of the homologous Arabidopsis cor15a gene and to a 5 bp core sequence in the low temperature- and dehydration-responsive elements (LTREs and DREs) identified in the promoter regions of several cold-responsive *Arabidopsis thaliana* genes. Mutation of either one or both of the GGCAC core sequence of the putative LTRE's to AATTC resulted in loss of cold-inducible gene expression, providing for the first time, direct evidence that CCGAC is required for low temperature expression. Furthermore, replacement of an enhancer region (–605 to –1107) of the promoter with a more active enhancer from the 35S constitutive cauliflower mosaic virus (CaMV) promoter resulted in a "hybrid" promoter with increased low temperature induced activity several fold over that of the native promoter.

18 Claims, 9 Drawing Sheets

| | |
|---|---|
| rd29A/lti78(DRE-1/LTRE-2) | t c a T A \| C C G A C \| A T c a g |
| rd29A/lti78(DRE-2/LTRE-3) | t a a T A \| C C G A C \| A T g a g |
| lti65(LTRE) | t g g A \| C C G A C \| T a a a |
| lti78(LTRE-1) | t g g A \| C C G A C \| T a c t |
| lti78(LTRE-4) | c a a G \| C C G A C \| A - a a a |
| cor15a(LTRE-1) | g t T G G \| C C G A C \| a t a c a |
| BN115(LTRE-1) | g t T G G \| C C G A C \| g t a t a |
| cor15a(LTRE-2) | c a T G G \| C C G A C \| c t g c t |
| BN115(LTRE-2) | g a T G G \| C C G A C \| c t g t t |

FIG. 1

-1262 TTAGAAAGTTTAAAATTTAATACTTGAACATGTGAAAGATTTTTCTTTTA
-1212 AAATATGATTTTAGAAAAAAATATATTATCTAATTTTTATTTATTTTAT
-1162 TATTAAAAACTGACATGTCACTACATATAACATGTAAATGAATAGTCATC
-1112 TTGCGGTCGACATTGAAAGATTCATGTTCTAAGATTTAGTTACAATTTGA
-1062 TGAACAAATAAGTTAAGTTTAAAGTTTTTTGCGATACAAATGTTAGGTTG
-1012 AAAGTTTAAAATGCTAATGAAAAACTTTAAAAGTTTAAAGTGTTAATGAA
-962 TACCACTTTGAGGGTTTTTATGCAATTTTATGCAATTTTCTCAATTTTTA
-912 AGTTACCCATCTAGGTACAAAAATATTTTAAACCATTTTGTCCAAGATTC
-862 GTGATTTCTTTGAGCCGGTCCTGATGGCTTGGCTCTGATGTACCAGAAAA
-812 TCGATGCACCACGCTAATATTTTGTACAAAAAAAAATCAATGTTATATAG
-762 CATTCAATGAAACGATTTAACCCATTTTGTAAATCCTAATTGAAAAAACT
-712 AATCTTGCACCCGGTGACCGTTATATATGCAACTTTGTGAAAATATGGTT
-662 TGTAGTTTTTATTTAAGCTATTACACCATGTCTGTTTAGAAGTTCCTAGT
-612 GGATAGGATATCTCTGAAAGTGACGTTAATTAATTGTTATTTATGTAATG
-562 GTATGCCTTTTAAAATTACAAAAATTGGTTTTAGTAGATAAATATGTTGT
-512 TTAAAGGAAAATAAATATAATGGTATGCCTTTTGAAATTACAAATATGAC
-462 GTTAATTAATTGTTATTTATGTAATGGAACCCCATGAAATACCATAAACC
-412 ATATATCACTCTATAAGTGTGATAGGCTTGCCATCATATACGTTATATTT
-362 TTATATCTATATTTTGAAAACTTTTTAGGCTTGCCATCATATACGTTTTT
-312 TTTTTTGGGGTAGATTTACTAACATGTTGGCCGACGTATACTTTTGTTT
-262 TTATCACAACAAAGGTGGTACACGTGAAGTAACGATAACGACCCACAACT
-212 CCGATTTCTTTGTGTTTAATTTTGCAAAAAATAAAAGCAGAAATGCTAAC
-162 ATGTATATCACCACAAGTTTTGATGGCCGACCTGTTTTTTCAATAGTTAA

FIGURE 2

```
-112 AGAAAATAACATCAATGCATTATAAAAAAATTCTACGATGCCACGTGATT
 -62 TGGATTGCAGTTGGTCTAGTATCTATAAAACTATGATACTATTGGAGAAT
 -12 AGATTATTACTCATCTCACTCTTGTTCCTATTAAAACTCCTCCTTTGATT
  39 TCTTTTGCTCGCTTTTGACTCTTTAAAGAGAACTTTCATGGCTATGTCAC
                                              M  A  M  S
  89 TCTCAGGATCAGCTGTTCTCATTGGGATTGGTTCTTCTTTCTCCAGCGGC
      L  S  G  S  A  V  L  I  G  I  G  S  S  F  S  S  G
 139 ATAGCCAAGCAGAGCGGCGTTGGCGCCGTCGGTTTTGGCCGGAAAACTGA
      I  A  K  Q  S  G  V  G  A  V  G  F  G  R  K  T  E
 189 GCTCGTCGTCGTCGCTCAGCGCAAGAAGTCGTTGATCTACGCCGATAAAG
      L  V  V  V  A  Q  R  K  K  S  L  I  Y  A  D  K
 239 GTGACGGCAACATTCTGGATGACCTCAATGAAGCCACGTAAGTCTAATCT
      G  D  G  N  I  L  D  D  L  N  E  A  T
 289 TATTCACCCAAAAACTCTCATATATATATATATTATTACTAACCATGATA
 339 TTACAATATCATTCAAGATATAGAGGTTCATAAACCATAATATATAATTG
 389 ATATCTCTTCTAATTTTTTAGTTTACATATTGACTCAAATATTTGAAAAT
 439 TAAGTAAGATACTTCCATGTTAGCCAATGTGGATATACGTTTTGTCAACA
 489 ATGAATCTGAATATACACATACATGAACAGAAAGAGAGCTTCGGATTACG
                                    K  R  A  S  D  Y
 539 CGACGGAGAAGACAAAGGAGGCGTTGAAAAATGGCGAGAAAGCAAAAGAC
      A  T  E  K  T  K  E  A  L  K  N  G  E  K  A  K  D
 589 TACGTTGTTGATAAGAACGTTGAAGCCAAAGACACTGCAGTGGATGAAGC
      Y  V  V  D  K  N  V  E  A  K  D  T  A  V  D  E  A
 639 TCAGAAAGCTTTGGATTATGTGAAGGCAAAAGGAAACGAAGCTGGGAACA
      Q  K  A  L  D  Y  V  K  A  K  G  N  E  A  G  N
 689 AAGTTGCCGAGTTTGTTGAGGGTAAAGCAGGAGAGGCTAAGGACGCCACA
      K  V  A  E  F  V  E  G  K  A  G  E  A  K  D  A  T
 739 AAAGCATGATGCTTCAACCACTTAACTCTAGATATATATATATATCTAGA
      K  A
 789 TTATCCTTGTTGTCTCATGTTTATTATTTTACAATAAGATCAGTTTGTTT
 839 AAAACTTCTATTTCACTAGTTGAAATAAAGATATGTTACTTAACTACTCA
 889 TCATTATATCTTGATGATGTCTTCAAAGTATATCAATGAGAAACTTAATA
 939 AAAGAGAACTTTTATGGA
```

FIGURE 2 CONTINUED

COLD INDUCED PROMOTER FROM WINTER *BRASSICA NAPUS*

FIELD OF INVENTION

This invention relates to the 5' regulatory region of a low-temperature-responsive gene from winter *Brassica napus*. This invention also relates to positive controlling elements within the regulatory region of the low-temperature-responsive gene from winter *Brassica napus*. This invention further relates to manipulation of structure and the use of this regulatory region, or sequences within the regulatory region, to control, by the reduction of temperature, the expression of genes.

BACKGROUND AND PRIOR ART

In plants capable of cold acclimation, growth at low, non-freezing temperatures leads to the acquisition of increased frost tolerance (Levitt, 1980 in *Responses of Plants to Environmental Stress. Chilling, Freezing and High Temperatures,* New York: 2nd Ed. Academic Press) and, in many species, to the accumulation of specific mRNAs. Low temperature-induced transcripts have been identified in several cold-acclimating species including spinach (Neven et al, 1993, Plant Mol Biol 21: 291–305), alfalfa (Laberge et al., 1993, Plant Physiol 101: 1411–1412; Wolfraim and Dhindsa, 1993, Plant Physiol 103: 667–668; Wolfraim et al., 1993, Plant Physiol 101: 1275–1282), barley (Catevelli and Bartels, 1990, Plant Physiol 93: 1504–1510; Hughes et al., 1992, Plant Cell Envir. 15: 861–865; Goddard et al., 1993, Plant Mol Biol 23: 871–879), wheat (Houde et al., 1992, Plant Physiol 99: 1381–1387; Chauvin et al., 1993, Plant Mol Biol 23: 255–265), Arabidopsis (Gilmour et al., 1992, Plant Mol Biol 18: 13–21; Kurkela and Franck, 1990, Plant Mol Biol IS: 137–144; Lång and Palva, 1992, Plant Mol Biol 20: 951–962; Nordin et al., 1991, Plant Mol Biol 16: 1061–1071, and Plant Mol Biol 21: 641–653, 1993) and *Brassica napus* (Orr et al., 1992a, Plant Physiol 98: 1532–1534 and 1992b, Plant Physiol 99: S-124; Weretilnyk et al., 1993, Plant Physiol 101: 171–177; Saez-Vasquez et al., 1993, Plant Mol Biol 23: 1211–1221).

For many of these transcripts, the corresponding clones have been isolated by differential screening of cDNA libraries and their sequences determined. Deduced amino acid sequences show that several of these low temperature-induced transcripts (Gilmour et al., 1992, Plant Mol Biol 18: 13–21; Houde et al., 1992, Plant Physiol 99: 1381–1387; Lång and Palva, 1992, Plant Mol Biol 20: 951–962; Neven et al., 1993, Plant Mol Biol 21: 291–305) encode peptides that are similar to those that accumulate during dehydrative stress, i.e. lea (late embryogenesis abundant) proteins (Baker et al., 1988, Plant Mol Biol 11: 277–291), dehydrins (Close et al., 1989, Plant Mol Biol 13: 95–108; Bartels et al., 1990, Planta 181: 27–34) and rab (responsive to ABA (abscisic acid)) proteins (Skriver and Mundy, 1990, Plant Cell 2: 503–512). It is generally thought that such proteins may help plants tolerate the cellular desiccation that accompanies extracelluar freezing. Indeed, both water stress (Siminovitch and Cloutier, 1982, Plant Physiol 69: 250–255) and ABA-application (Chen and Gusta, 1983, Plant Physiol 73: 71–75) at non-acclimating temperatures can induce increased freezing tolerance, and accumulation of proteins encoded by two spinach genes responsive to drought and low temperature was shown to be initiated by a change in the hydration state of the plant tissue (Guy et al., 1992, Planta 188: 265–270). Other cold-induced transcripts encode peptides that are enriched in alanine or glycine (Gilmour et al., 1992, Plant Mol Biol 18: 13–21; Kurkela and Franck, 1990, Plant Mol Biol 15: 137–144; Orr, et al., 1992a, Plant Physiol 98: 1532–1534), or enriched in alanine, lysine and arginine with homology to the human tumor gene bbc1 (Saez-Vasquez et al., 1993, Plant Mol Biol 23: 1211–1221). Still others have been shown to share homologies with LIP, a lipid transfer protein (Hughes et al., 1992, Plant Cell Envir. 15: 861–865) or with the translation elongation factor la (Dunn et al., 1993, Plant Mol Biol 23: 221–225). In most cases, these low temperature-induced transcripts are also induced, often to a lesser degree, by ABA (abscisic acid) (Hajela et al., 1990, Plant Physiol 93: 1246–1252; Kurkela and Frank, 1991, Plant Mol Biol 15: 137–144; Lång and Palva, 1992, Plant Mol Biol 20: 951–962; Neven et al., 1993, Plant Mol Biol 21: 291–305; Nordin et al., 1991, Plant Mol Biol 16: 1061–1071). Endogenous ABA levels have been observed to increase transiently during the cold acclimation process in potato (Chen et al., 1983, Plant Physiol 73: 362–365) and spinach (Guy and Haskell, 1988, Electrophoresis 9: 787–796).

The isolation and characterization of cDNA clones of three related cold-induced transcripts, pBN115, pBN19 and pBN26 from winter *B. napus* cv. Jet neuf have recently been reported (Weretilnyk et al., 1993, Plant Physiol 101: 171–177). Transcripts hybridizing to pBN115 accounted for 0.15% of the mRNA in the leaves of cold-treated Jet neuf plants. BN115 transcripts did not accumulate in ABA-treated leaves or in the roots and mature seeds of cold treated winter *B. napus* plants (Weretilnyk et al., 1993, Plant Physiol 101: 171–177). The nucleotide and deduced amino acid sequences of pBN11S (and its relatives) are similar to those of cor15a and cor15b, two low temperature induced genes from *Arabidopsis thaliana* (Lin and Thomashow, 1992, Plant Physiol 99: 519–525; 100: 546–547(correction); Wilhelm and Thomashow, 1993, Plant Mol Biol 23: 1073–1077). Unlike BN1S, probes prepared from the cor15 cDNA clone hybridize to both low temperature- and ABA-inducible transcripts (Hajela et al., 1990, Plant Physiol 93: 1246–1252). The first 50 amino acids of BN115 and COR15 show similarities to chloroplast targeting sequences and it has been shown that a processed COR15 peptide of approximately 9 kDa is present in the stromal fraction of cold-acclimated *A. thaliana* chloroplasts (Lin and Thomashow, 1992, Plant Physiol 99: 519–525; 100: 546–547(correction)).

The regulation of gene expression by low temperature is critical to understanding the process of cold acclimation in plants. Cold-induced genes have been shown to be regulated by separate ABA independent and dependent pathways on exposure to low temperatures (Gilmour and Thomashow, 1991, Plant Mol Biol 17: 1233–1240; Nordin et al., 1991, Plant Mol Biol 16: 1061–1071). The low temperature regulation, at the transcriptional level, of one of these genes has been demonstrated in transgenic Arabidopsis (Yamaguchi-Shinozaki and Shinozaki, 1993, Mol Gen Genet 236: 331–340; Horvath et al., 1993, Plant Physiol 103: 1047–1053) and cis elements involved in drought regulation have been identified, although the exact elements responsible for cold have not been demonstrated unequivocally (Yamaguchi-Shinozaki and Shinozaki, 1994, Plant Cell 6: 251–264). In order to understand low temperature regulation of gene expression in winter *B. napus*, the genomic clone of BN115 was isolated, sequenced and the promoter region studied by the transient expression of the GUS (β-glucuronidase) reporter gene from the BN115 promoter following microprojectile bombardment of *B. napus,* cv. Jet neuf leaves. The development of a reliable transient expression system for the study of gene regulation in B. napus is useful as, to date, Agrobactenum-mediated procedures developed for B. napus transformation have been found to be relatively inefficient (Radke et al., 1988, Theor Appl Genet 75: 685–694; Charest et al., 1988, Theor Appl Genet 75: 438–445) making it difficult to generate homozygous transformants required for detailed promoter analysis. Transient expression systems using rice protoplasts have proven successful for the identification of the regulatory elements required for ABA-mediated expression of the wheat Em (Marcotte et al., 1989, Plant Cell 1: 969–976) and maize rab28 (Pla et al., 1993, Plant Mol Biol 21: 259–266) genes. We have chosen to study the 5' regulatory regions of BN115 in particular as the gene is transcriptionally regulated, responds rapidly to low temperature (resulting in the appearance of BN115 transcripts within one day of cold treatment), but does not respond to exogenous applications of ABA at 20° C. (Weretilnyk et al., 1993, Plant Physiol 101: 171–177). In addition, BN115 transcripts are the most abundant of those induced by low temperature in the leaves of winter B. napus that we have identified so far.

In this application, we demonstrate the ability of the regulatory region of BN115 to direct gene expression at low temperature and provide direct identification of regions containing potential cis-elements involved in this regulation in B. napus. The cold induced promoter of the present invention is not ABA inducible, which distinguishes it from other cold induced promoters of the prior art. Furthermore, we provide evidence that cold-induction of gene expression by the promoter could be enhanced by the construction of a "hybrid" promoter with a more powerful enhancer.

SUMMARY OF INVENTION

The present invention is directed to the 5' regulatory region of a low-temperature-responsive gene, BN115, from winter Brassica napus. A 1.2 kb promoter fragment (bp −1107 to +100 of FIG. 2; 156 to 1362 of SEQ ID NO:1) was fused to the GUS reporter gene and found to direct low-temperature expression of GUS in transgenic B. napus seedlings. Thus the present invention is directed to a low-temperature induced promoter from winter Brassica napus.

Deletions, mutations and substitutions within the BN115 promoter were used to identify cis elements and enhancers involved in the low-temperature regulation of BN115 expression. The region between bp −1107 and −802 (of FIG. 2; 156 to 461 of SEQ ID NO:1) contain an enhancer element for low-temperature expression. This enhancer can be substituted for a stronger enhancer, for example, from the 35S constitutive cauliflower mosaic virus (CaMV) promoter to provide increased low temperature induced activity. A 5 bp repeat, CCGAC, was identified as the basic low-temperature regulatory element or LTRE.

This invention is thus directed to controlling elements within the promoter region.

This invention is further directed to the use of the promoter or sequences within the promoter to control, by the reduction of temperature, the expression of genes.

Thus, according to the present invention, there is provided a DNA molecule, or an analog thereof, comprising a 5' regulatory region of a low-temperature-responsive gene, BN115, from Brassica napus.

Further, according to the present invention, there is provided a DNA molecule, or an analog thereof, comprising a 5' regulatory region of a low-temperature-responsive gene, BN115, from Brassica napus, wherein said molecule comprises one or more of a low-temperature regulatory element comprising the sequence CCGAC.

The present invention is further directed to a cold inducible promoter from Brassica napus.

This invention is further directed to a use of a cold inducible promoter from Brassica napus to control by the reduction of temperature the expression of a gene.

BRIEF DESCRIPTION OF THE DRAWINGS

FIG. 1 shows the alignment of the LTREs (low-temperature-responsive element) and DREs (dehydration-responsive element) from the Arabidopsis rd29A (lti78), lti65 and cor15a genes with the TGGCCGAC direct repeat from the BN115 promoter. The drought and low temperature responsive elements from rd29A (Yamaguchi-Shinozaki and Shinozaki, 1994, Plant Cell 6: 251–264), putative low temperature responsive elements from lti78, lti65 (Nordin et al., 1993, Plant Mol Biol 21: 641–653), cor15a (Baker et al., 1994, Plant Mol Biol 24: 701–713) genes, and the corresponding BN115 sequences are shown. Upper case letters indicate repeated or conserved nucleotides within each gene. For genes containing more than one LTREs, #1 designates the 5'-most element.

FIG. 2 shows the genomic sequence of BN115, SEQ ID NO: 1. The location of the direct repeats of 31, 22 and 8 bp are indicated by solid, striped or unfilled bars, respectively, above the corresponding nucleotide sequences. The two G-boxes are boxed in and the putative TATA box and polyadenylation signals are underlined. The start of transcription, as determined by primer extension analysis, is designated with an asterisk. The deduced amino acid sequences for the protein coding regions are given below the corresponding nucleotide sequences.

by a gain-of-function experiment in bombarded Brassica leaves. DNA sequences from −300 to −53 (of FIG. 2; 963 to 1210 of SEQ ID NO:1) of the BN115 promoter were amplified by PCR and inserted upstream of the CaMV (cauliflower mosaic virus) 35S promoter truncated to −46. pEMBL46GUS3C and the −300/−46GUS fusion plasmids were introduced, along with the internal standard plasmid pEPLUX, by biolistic bombardment. Histogram shows the relative GUS/luciferase activity ratios measured for each of these two constructs in bombarded Jet neuf leaves after 24–48 h incubation at 2° C., 22° C. and 22° C. plus ABA. All activity ratios were normalized to that of the full-length promoter/GUS construct at 2° C. set at 100%. Values shown represent the average of the GUS/net LUX activity (in nmol MU produced $min^{-1}$ $mg^{-1}$/$mVsec^{-1}$ $\mu g^{-1}$) determined for 2 independent experiments as described in the Examples. The activity of the −300 deletion under the 3 incubation conditions is shown for comparison. Fined circles represent the G-boxes, open circles represent the 8 bp motif TGGC-CGAC. The open and shaded rectangles represent the truncated BN115 and CaMV promoters, respectively.

Figure 7:
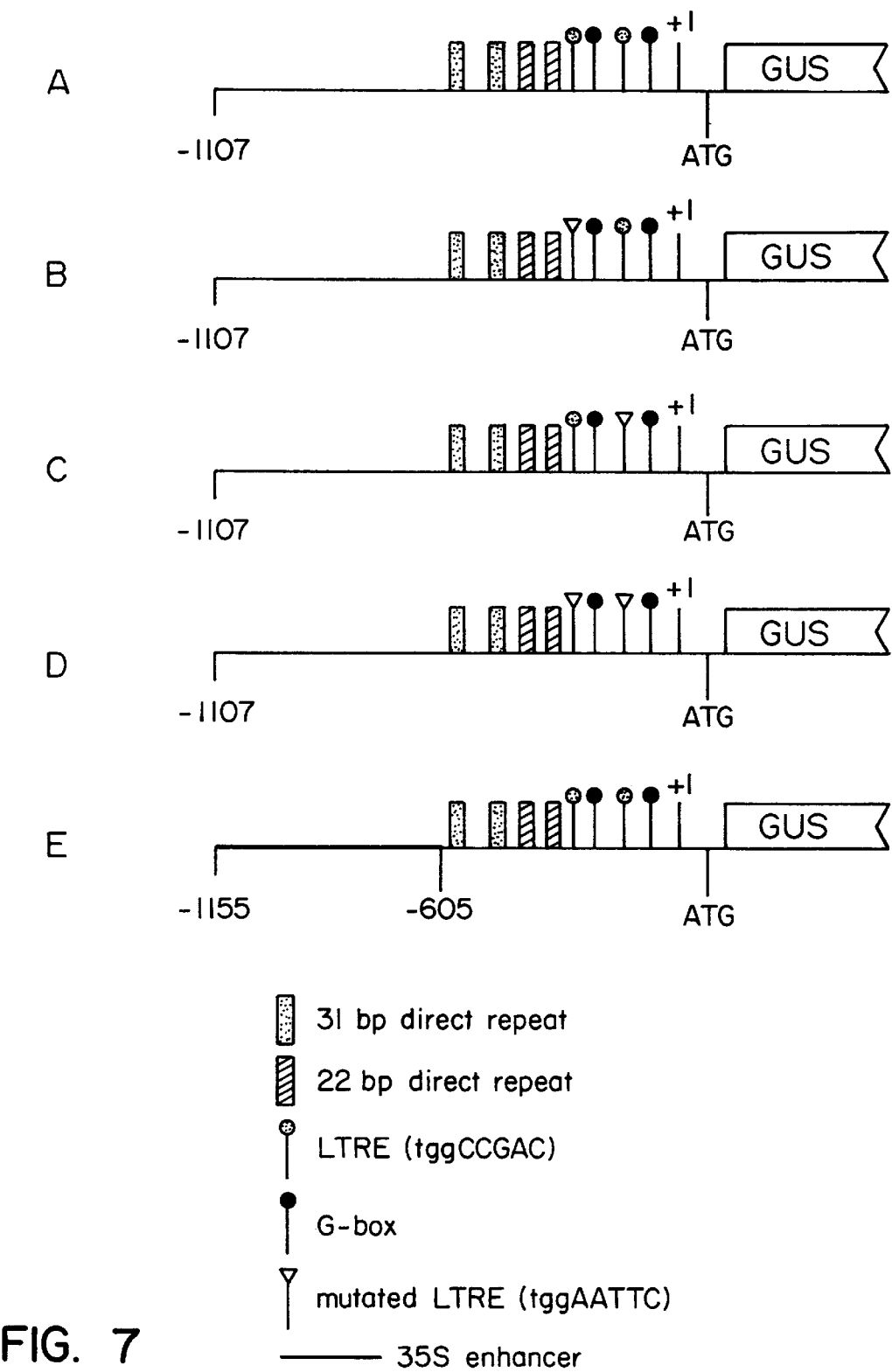

FIG. 7 shows the linear maps of the promoter indicating mutation and replacement of specific domains affecting low temperature induced gene expression.

Figure 8:
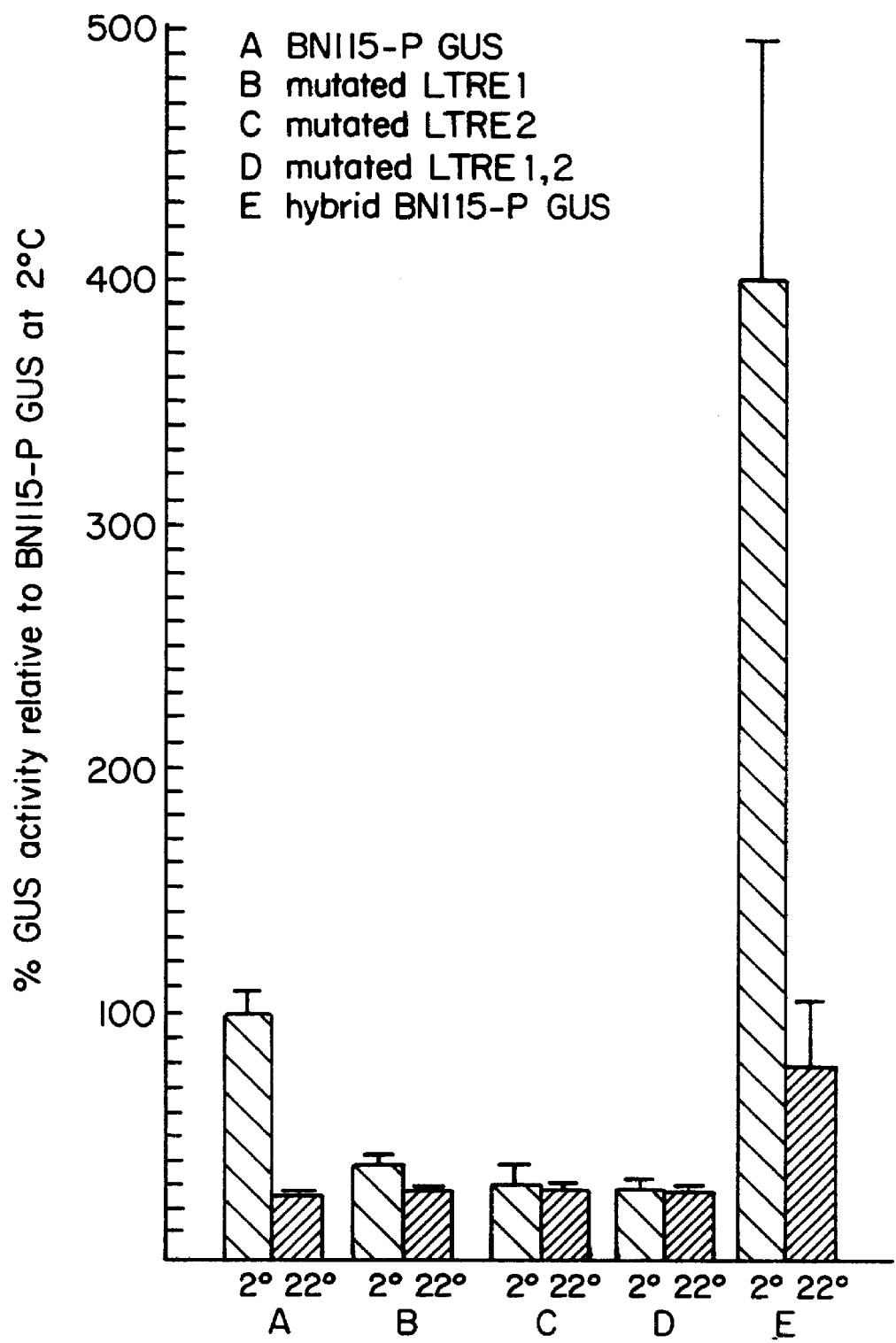

FIG. 8 shows the effect of mutation and replacement of the sequences as indicated in FIG. 7 on cold-induced gene expression. Note that mutation of the CCGAC sequence to AATTC in each or both of the repeat resulted in loss of cold-induced transient expression after microprojectile bombardment with the constructs as outlined in FIG. 6. Note also that replacement of the putative enhancer region of the promoter with the enhancer from the cauliflower mosaic virus 35S promoter resulted in several-fold increase in cold-induced gene expression. This allows for the construction of a stronger cold-inducible promoter.

DETAILED DESCRIPTION OF THE PREFERRED EMBODIMENTS

The 5' regulatory region of a low temperature regulated gene, BN115, from winter *Brassica napus* L. cv Jet neuf was isolated, sequenced and characterized. A 1.2 kb promoter fragment (bp −1107 to +100 of FIG. 2; 156 to 1362 of SEQ ID NO:1) was fused to the GUS (β-glucuronidase) reporter gene and found to direct the low temperature- but not ABA-regulated expression of GUS in photosynthetic tissues of transgenic *B. napus* seedlings. No GUS expression was detected in any of the transgenic seedlings incubated at 22° C., either in the presence or in the absence of ABA The GUS reporter gene was used to demonstrate the low-temperature inducibility of the BN115 5' regulatory region. Any other convenient marker gene could have been used to demonstrate the activity of this regulatory region.

Transient GUS expression from the BN115 promoter was also determined in leaves bombarded with the plasmid pUC119/115P-GUS, containing bp −1107 to +100 (of FIG. 2; 156 to 1362 of SEQ ID NO:1) of the 5' regulatory region of BN115 fused in frame to the GUS gene. GUS expression was approximately 5-fold higher in bombarded leaves incubated at 2° C. for 48 hours than at 22° C. under the same conditions. These two independent experiments thus support the presence of a low-temperature inducible promoter within the 5' regulatory region of BN115.

Transient expression of the GUS reporter gene in microprojectile-bombarded Jet neuf leaves from a series of plasmids with increasingly larger 5' deletions in the BN115 promoter was used to identify regions containing potential cis-elements involved in the low temperature regulation of BN115 expression. The region between bp −1107 to −802 of FIG. 2; 156 to 461 of SEQ ID NO:1) in the BN115 promoter is an A/T-rich region that appears to contain an enhancer element for low temperature expression. Deletion of this region resulted in a 40% decrease in the activity of the BN115 promoter at 2° C. but had no effect on its activity at 22° C. The next 162 bp (−802 to −640 of FIG. 2; 461 to 623 of SEQ ID NO:1), in addition to containing sequences that enhance BN115 promoter activity at 2° C., may also contain possible negative regulatory elements (NREs) that repress gene expression at 22° C. Deletion of this region resulted in an increase in BN115-promoted GUS expression in bombarded Jet neuf leaves at 22° C. Deletion of the regions of the BN115 promoter containing the 31 bp direct repeat (−640 to −436 of FIG. 2; 623 to 827 of SEQ IS NO:1) and the 22 bp direct repeat (434 to −302 of FIG. 2; 829 to 961 of SEQ ID NO:1) results in almost no change in promoter activity at both 2° C. and 22° C.

Deletion of the next 28 bp (to −274 of FIG. 2; 989 of SEQ ID NO:1) markedly decreases transient expression at 2° C. to a level below that at 22° C. for the first time without affecting expression at 22° C. in bombarded leaves. Contained within this 28 bp fragment is the first half of an 8 bp direct repeat, TGGCCGAC, that may contain the basic low temperature regulatory element or LTRE. This 8 bp motif, also found repeated in the promoter of cor15a (Baker et al., 1994, Plant Mol Biol 24: 701–713) is similar to the repeated sequence G/TA/GCCGACA/TT/A-A/T present in the promoter regions of three low temperature induced genes from *A. thaliana*: rab18 (Lång and Palva, 1992, Plant Mol Biol 20: 951–962), lti78 and lti65 (Nordin et al., 1993, Plant Mol Biol 21: 641–653) FIG. 1). Yamaguchi-Shinozaki and Shinozaki 1994, Plant Cell 6:251–264) have identified a 9 bp core sequence, TACCGACAT, within a 20 bp repeated sequence in the rd29A (lti78) promoter as a dehydration responsive element (DRE). While mutational analysis was used to demonstrate directly the requirement of this motif for response to drought, the importance of this to cold was only inferred from deletion studies which showed that a 71 bp fragment containing this 9 bp core was able to direct cold-induced gene expression. In this application, the involvement of CCGAC in cold-induced gene expression was demonstrated directly by mutation of the motif.

Furthermore, it is demonstrated that substitution of the enhancer region (−1107 to −705 of FIG. 2; 156 to 658 of SEQ ID NO:1) with a stronger enhancer from the CaMV 35S promoter resulted in increased cold inducible promoter activity. The effect of any enhancer domains on cold inducibility in rd29A was not demonstrated (Yamaguchi-Shinozaki and Shinozaki, 1994, Plant Cell 6: 251–264)

Thus, the present invention includes a DNA sequence comprising the 5' regulatory region of the BN115 gene from *B. napus*, cis-acting and enhancer elements within this region and analogs, thereof. Analogs of the 5' regulatory region or the cis-acting elements within this region include any substitution, deletion, or additions of the region, provided that said analogs maintain the low-temperature promoter activity or the activity of the other cis-acting elements.

The DNA sequence of the present invention thus includes the DNA sequence of SEQ ID NO: 1 and those DNA sequences which hybridize under stringent hybridization conditions (see Maniatis et al., in Molecular Cloning (A Laboratory Manual), Cold Spring Harbor Laboratory (1982) p 387 to 389) to the DNA sequence of SEQ ID NO: 1, provided that said sequences maintain the low-temperature promoter activity or the activity of the other cis-acting elements. An example of one such stringent hybridization conditions may be hybridization at 4×SSC at 65° C., followed by washing in 0.1×SSC at 65° C. for an hour. Alternatively an exemplary stringent hybridization condition could be in 50% formamide, 4×SSC at 42° C. Also included within the scope of the present invention are DNA sequences which hybridize to the sequence of SEQ ID NO: 1 under relaxed hybridization conditions, provided that said sequences maintain the low-temperature promoter activity or the activity of the other cis-acting elements. Examples of such non-hybridization conditions includes hybridization at 4×SSC at 50° C. or with 30–40% formamide at 42° C.

Another aspect of the present invention includes the use of the cold-inducible promoter to control expression of various genes by temperature. The present invention is also directed to the use of enhancer sequences, which enhances the expression of a gene at low temperatures.

While this invention is described in detail with particular reference to preferred embodiments thereof, said embodiments are offered to illustrate but not limit the invention.

EXAMPLES

Isolation of the BNI15 Genomic Clone

Winter *Brassica napus* L cv Jet neuf and Spring *B. napus* cv. Westar were grown in controlled environment growth chambers at 22° C under a 16-h, 250 μE m7$^2$ s$^{-1}$ light intensity day and an 8-h, 20° C. night.

Seeds of winter *B. napus* cv Jet neuf were surface-sterilized with 3% sodium hypochlorite and germinated in the dark at room temperature on sterile, moistened filter paper in sterile glass trays. DNA was isolated from 25 g of dark-grown cotyledons as described in Unit 2.3 of *Current Protocols in Molecular Biology* (1987) except that 2% SDS was used in place of 10% Sarkosyl and the DNA was extracted with 1 vol each of phenol saturated with extraction buffer and chloroform before the initial precipitation with ethanol. High molecular weight DNA was partially digested with BamHI and the fragments fractionated by sucrose gradient centrifugation (Unit 5.3-*Current Protocols in Molecular Biology*, 1987). Fractions containing DNA fragments of 9 to 20 kb in length were pooled, purified (Unit 5.3-*Current Protocols in Molecular Biology*, 1987) and ligated to the arms of the vector λ DASH (Stratagene, LaJolla, Calif.). The library was packaged using the Gigapack II Gold packaging extract (Stratagene) and transfected into the McrA-, McrB- *E. coli* host strain WA802 (Wood, 1966, J Mol Biol 16: 118–133). The library was screened with a digoxigenin-dUTP labelled probe prepared from the pBN115 cDNA clone (Weretilnyk et al., 1993, Plant Physiol 101: 171–177) using the Nonradioactive DNA Labeling and Detection Kit (Boehringer Mannheim, Germany) according to the manufacturer's protocol. Positive clones were visualized by immunological detection with anti-Dig-dUTP/alkaline phosphatase conjugate using p-nitroblue tetrazoliunm chloride and 5-bromo-4-chloro-3-indoyl-phosphate (p-toluidine salt) as substrates following the manufacturer's instructions. A genomic clone containing a 7.0 kb BamHI fragment hybridizing to pBN115 was isolated and the fragment subcloned into pUC119 (Yanisch-Perron et al., 1985, Gene 33: 103–119). A 3.0 kb XbaI fragment containing the entire coding region, a single 0.26 kb intron, and over 2 kb of the 5' regulatory region was further subcloned into pUC119 in both orientations (pUC119-G28 and pUC119-G29) for sequencing.

The sequence of this genomic subclone of BN115, which is 100% identical in the protein coding regions to the cDNA clone pBN115 (Weretilnyk et al., 1993, Plant Physiol 101: 171–177), is shown in FIG. 2. The transcriptional start site of BN115 was determined by primer extension analysis (Sambrook et al., 1989, *Molecular Cloning: A Laboratory Manual*, Second Edition. New York: Cold Spring Harbor Laboratory Press) as follows: 20 μg of total RNA isolated from the leaves of room temperature or 4-day cold-treated winter *B. napus* was hybridized to a $^{32}$P-labelled oligonucleotide DNA probe 5'-GAACAGCTGATCCIGAGAGTGACATAGCCATG-3' (complementary to bp +75 to +106 of FIG. 2; 1337 to 1368 of SEQ ID NO:1) and the DNA extended with AMV reverse transcriptase (Pharmacia, Milwaukee, Wis.). Extension products were resolved on a 6% denaturing polyacrylamide gel alongside sequencing reactions performed using the same primer and compared to sequences produced from the 5' end of the BN115 gene (results not shown). The putative TATA box (TATAAA) is located from −39 to −35 (of FIG. 2; 1224 to 1228 of SEQ ID NO:1) and putative polyadenylation signals (AATAAA) at +935 to +940 (of FIG. 2; 2124 to 2129 and 2197 to 2202 of SEQ ID NO:1).

Analysis of the 5' regulatory region showed that it contains two large direct repeats of 31 bp (−592 to −562 and −466 to −436 of FIG. 2; 671 to 701 and 797 to 827 of SEQ ID NO:1) and 22 bp (−390 to −369 and −337 to −316 of FIG. 2; 873 to 894 and 926 to 947 of SEQ ID NO:1) and several smaller direct repeats, including an 8 bp direct repeat (TGGCCGAC) located at bp −284 to −277 and −139 to −132 (of FIG. 2; 979 to 985 and 1124 to 1131 of SEQ ID NO:1). An identical 8 bp direct repeat is present within the similar region of the promoter of the homologous *A. thaliana* cor15a gene, a region found to be sufficient to direct the low temperature-responsive expression of GUS in transgenic Arabidopsis (Baker et al., 1994, Plant Mol Biol 24: 701–713). The last five base pairs are also found within repeated sequences (G/TA/G A A/TT/A) observed in regulatory sequences of low temperature regulated genes lti78 (rd29A) and lti65 (rd29B) from *Arabidopsis thaliana*. (Nordin et al., 1993, Plant Mol Biol 21: 641–653; Yamaguchi-Shinozaki and Shinozaki, 1994, Plant Cell 6: 251–264).

Two G-boxes (Guiliano et al., 1988, Proc Natl Acad Sci USA 85: 7089–7093) are present in the BN115 promoter (bp −242 to −237 and bp −71 to −66) and are staggered with the 8 bp repeat (FIG. 1). Although the core hexamer of these two G-boxes (CACGTG) is the same as those found in some ABA-responsive elements (ABREs) (Marcotte et al., 1989, Plant Cell 1: 969–976), the flanking nucleotides are not. The observation that no ABA-inducible transcripts were found to hybridize to pBN115 (Weretilnyk et al., 1993, Plant Physiol 101: 171–177), and that no ABA-induced GUS expression was observed in plants transformed with the BN115 promoter (data below) suggests that the two G-boxes in the BN115 promoter are probably not functioning as ABREs.

BN115-Promoted GUS Expression in Transgenic *B. napus* Plants

Figure 3:
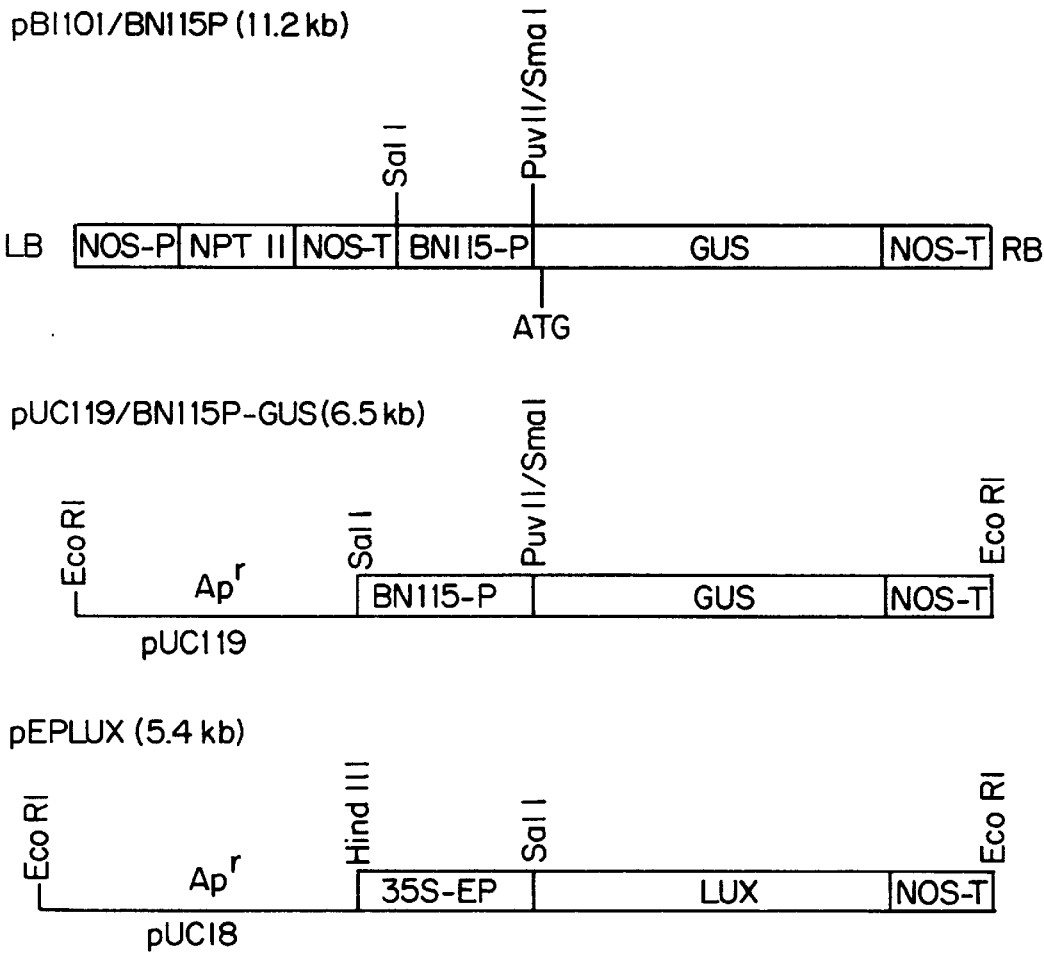
FIG. 3 shows the plasmids used for microprojectile bombardments and transformations. The plasmids pBI101/BN11SP-GUS, pUC119/BN115P-GUS and pEPLux were constructed as described in the Examples. The relevant restriction sites used for the constructions are shown. BN115-P represents the promoter, Ap$^r$ represents the β-lactamase gene present in the plasmid vectors pUC119 and pUC18. NPTII represents the neomycin phosphotransferase gene which confers resistance to kanamycin in the transgenic plants. NosP and NosT represent the nopaline synthase promoter and 3'-termination sequences respectively.

A 2.1 kb fragment containing the GUS coding region and the nopaline synthase (nos) terminator was isolated from the binary vector pBI101.2 (Jefferson, 1987, Plant Mol Biol Rep 5: 387–405) by HindIII/EcoRI digestion and inserted into the polylinker of pUC119 (Yanisch-Perron et al., 1985, Gene 33: 103–119) to generate pUC119-GUSter. A 1.2 kb SalI/PvuII fragment of the genomic BN11S subclone was then ligated to pUC119-GUSter that had been digested with SalI and SmaI. This generates the plasmid pUC119/115P-GUS (FIG. 3) encoding an in-frame fusion protein of which the first eight amino acids are those encoded by BN115. The plasmid pEPLux, which expresses the firefly luciferase gene under the control of an enhanced CaMV 35S promoter and serves as an internal standard for each bombardment, was constructed by replacing the 0.5 kb HindIII/SalI CaMV 35S promoter fragment in pJD300 (Luehrsen et al., 1992, *Methods in Enzymology* 216, 397–414 (Wu, R., ed). San Diego: Harcourt Brace Jovanovich) with a 0.8 kb fragment containing the CaMV 35S enhancer and promoter sequences excised from the plasmid pFF19G (Timmermans et al., 1990, J Biotech 14: 333–344) by digestion with HindIII and SalI. For *Agrobacterium tumefaciens*-mediated transformation of spring *B. napus* cv. Westar, the 1.2 kb SalI/PvuII fragment containing the BN115 promoter was inserted into the polylinker of the binary plasmid pBI101.2 (Jefferson, 1987, Plant Mol Biol Rep 5: 387–405) which had been digested with SalI and SmaI, to generate pBI101.115 GUS (FIG. 3).

Plasmid, pBI101/BN115P-GUS, was introduced into spring *B. napus* cv. Westar via *Agrobacterium tumefaciens*-mediated transformation, essentially using the method of Moloney et al., 1989, Plant Cell Rep 8: 238–242. The spring cultivar was used as the host because transformation protocols for *B. napus* are found to be genotype- (Charest et al., 1988, Theor Appl Genet 75: 438–445; De Block et al, 1989, Plant Physiol 91: 694–701) and/or laboratory-dependent (Fry et al., 1987, Plant Cell Rep 6: 321–325; Radke et al., 1988, Theor Appl Genet 75: 685–694) with winter varieties being particularly difficult to transform. It is expected that the spring cultivar will regulate the BN115 promoter under low temperatures as the winter type since the spring cultivar does develop increased frost tolerance during cold acclimation (Laroche et al., 1992, Plant Cell Environ 15: 439–445) and, more importantly, it does accumulate transcripts hybridizing to BN115 in response to low temperature exposure (Weretilnyk et al., 1993, Plant Physiol 101: 171–177).

Cotyledons and petioles of spring *B. napus* cv. Westar were co-cultured with the *A. tumefaciens* strain GV3101/pMP90 carrying the binary plasmid pBI101/BN115P-GUS (FIG. 3). Following a 7 days recovery, positive primary transgenics were isolated by selection on 25 mg/l kanamycin and were rooted on media containing 0.5/L each of α-napthaleneacetic acid (NAA) and indole-3-acetic acid (IAA). Selfed seeds, collected from these primary transgenics were germinated in Magenta boxes on MS agar (Murashige and Skoog, 1962, Plant Physiol 15: 473–497) containing 100 mg/l kanamycin and reselected. Resistant progeny from these were selfed and the seeds obtained were again subjected to another round of germination and selection on 100 mg\1 kanamycin to identify homozygous lines. Ten seeds from each independent transgenic line were germinated on MS agar (minus kanamycin) in Magenta boxes and placed at 22° C. under 16-h, 250 $\mu$E m$^{-2}$ s$^{-1}$ light intensity day. Seedlings (5 cm tall and containing the cotyledons and first two leaves) were either transferred to 2° C., same light intensity, left at 22° C. or transferred to new media containing 10$^{-4}$ M ABA at 22° C. for 72h. After 3 days, the whole seedlings were assayed for GUS expression following incubation in 5-bromo-4-chloro-3-indoyl glucuronide for 2h or overnight as described by Jefferson (1987), Plant Mol Biol Rep 5: 387–405. The seedlings were then bleached in a solution of ethanol:propionic acid (3:1 v/v) and rinsed with 70% ethanol.

Figure 4:
FIG. 4 shows the effect of cold on the B. napus cv Westar seedlings transformed with pBl101/BN115P-GUS. The seedlings were grown on sterile MS agar, incubated for 72 hours at 2° C. (left) and 22° C. (right), and then stained with GUS overnight and cleared of chlorophyll.

Transgenic *B. napus* seedlings show strong BN115-promoted GUS expression after incubation for 72 h at 2° C., but not at 22° C. (FIG. 4). Seedlings from seeds of 5 independent transformants were analyzed for low temperature induced GUS expression. All of these showed BN115-promoted GUS activity at low temperature. No GUS expression was detected in any of the transgenic seedlings incubated at 22° C., either in the presence or absence of ABA, even after an overnight incubation in the histochemical assay solution (results not shown). Non-transformed control plants did not show GUS expression at either temperature (data not shown). Microscopic analysis of the leaves of cold-treated seedlings stained for GUS expression showed that BN115-promoted GUS expression occurs primarily in the mesophyll cells with little or no expression in the epidermis or trichomes (results not shown).

Assay of BN115 Promoter Activity by Transient GUS Expression in Bombarded Winter *B. napus* L. cv Jet neuf Leaves Young, expanding *B. napus* cv Jet neuf leaves (grown at 22° C. as described above) were cut, sterilized first in 70% ethanol (30 sec) and then in 1.4% calcium hypochlorite (plus a drop of Tween 20) for 4 min, rinsed three times with sterile distilled water and mounted on MS media (Murashige and Skoog, 1962, Plant Physiol 15: 473–497) containing 3% sucrose and 0.6% phytagar in 35×10 mm petri dishes (one leaf per dish). After an overnight incubation in a controlled environment growth chamber set at 250 $\mu$Em$^{-2}$s$^{-1}$ with a 16 h photoperiod (22° C. light and 20° C. dark), leaves were bombarded at 900 psi with 1.6 $\mu$m gold particles coated with a mixture of pEPLux plasmid and BN115 promoter deletion/GUS fusion plasmid at a ratio of 1:4 (w:w) using the Biolistic PDS-1000/He system particle gun (Bio-Rad, Hercules, Calif.) as follows: 5 $\mu$g DNA in 5 $\mu$l TE (10 mM Tris, pH8 and 1 mM EDTA) was combined (while vortexing) with 50 $\mu$l suspended gold particles, 50 $\mu$l 2.5 M CaCl$_2$ and 10 $\mu$l 0.1 M spermidine; particles were allowed to settle for 10 min at RT, washed twice with 200 ,l ethanol and resuspended in 30 $\mu$l ethanol; 5 $\mu$l of resuspended DNA-coated gold particles were pipetted onto six flying discs which were used to bombard six individually mounted leaves.

Four of six leaves bombarded with a given deletion plasmid+pEPLux were transferred to semi-solid MS media in 60×15 mm petri dishes and the other two transferred to semi-solid MS media containing 100 $\mu$M (±)ABA. Two of the four leaves mounted on MS media and the two leaves mounted on ABA-containing MS media were incubated for 24 or 48 hours in the same controlled environment growth chamber as above. The remaining two leaves mounted on MS media were incubated for 24 or 48 hours in another chamber set at 2° C. (constant) and approximately the same light intensity and 16 h light period. Leaves continued to expand throughout the above manipulations. At least 3 sets of six leaves each were bombarded with each promoter deletion+pEPLux and no difference in the relative promoter activity was observed when incubating for either 24 or 48 hours under any of the individual conditions. Under the conditions used, the bombarded leaves suffered very little visible damage and continued to expand throughout the mounting, bombardment and subsequent incubation procedures.

Histochemical detection of GUS activity was performed as described by Jefferson (1987), Plant Mol Biol Rep 5:387–405, using 5-bromo-4-chloro-3-indoyl glucuronide (Sigma, St. Louis, Mo.) as substrate. To facilitate visualization of blue spots, the leaves were bleached in ethanol:propionic acid (3:1 v/v) and rinsed with 70% ethanol. For fluorimetric GUS and luciferase assays, a single extract was prepared from one or two leaves from each treatment by homogenizing in 1.5–2.0 ml extraction buffer (100 mM potassium phosphate pH 7.8, 1 mM Na$_2$EDTA, 10% glycerol, 7 mM β-mercaptoethanol) and clearing by centrifugation (15 min at 4° C. in a microfuge). GUS activity in the supernatant was measured fluorimetrically using 4-methyl umbelliferyl β-D-glucuronide (Sigma) as substrate (Jefferson, 1987, Plant Mol Biol Rep 5: 387–405). Luciferase (LUX) activity was measured as follows: 20 μl extract was added to 200 μl assay buffer (25 mM Tricine pH 7.8, 15 mM MgCl$_2$, 5 mM ATP, 7 mM β-mercaptoethanol, 1 mg ml$^{-1}$ bovine serum albumin) in the sample cuvette and placed in the LKB 1250 Luminometer (LKB-Wallac, Finland) equilibrated to 25° C. The reaction was initiated by injection of 100 μl of 0.5 mM luciferin (Analytical Luminescence Laboratory, San Diego, Calif.) into the sample cuvette and the luminescence (in mV) integrated over a 10 sec interval. Protein concentrations were determined according to the method of Bradford (1976), Anal Biochem 72: 248–254, using IgG as standard. For each extract (prepared from one or two bombarded leaves), the GUS activity (in nmol methyl umbelliferone (MU) produced min$^{-1}$ mg$^{-1}$) and LUX activity (in mVsec$^{-1}$ μg$^{-1}$) of control extract from a non-bombarded leaf was subtracted from the total observed GUS and LUX activities before calculating the ratio. The GUS/LUX activity ratios (in nmol MU produced min$^{-1}$ mg$^{-1}$/mVsec$^{-1}$ μg$^{-1}$) represent the average (±standard error) of at least three independent extracts each prepared from one or two leaves bombarded with one deletion construct+pEPLUX and incubated under one of the three incubation conditions.

Histochemical staining for transient GUS activity in Jet neuf leaves bombarded with pUC119/BN115P-GUS resulted in approximately ten-fold more blue spots being observed in the leaves that had been incubated for 48 h at 2° C. than in the leaves that had been incubated at 22° C. on the same media plus or minus 100 μM ABA (results not shown).

Analysis of 5' Deletions in the BN115 Promoter

In order to identify regions containing the cis-acting elements involved in regulating the low temperature expression of BN115 in B. napus cv Jet neuf, a series of seven nested deletions from the 5' end of the promoter region was constructed. Nested deletions from both the 5' and 3' ends of the XbaI genomic subclone and from the 5' end of the BN115 promoter/GUS fusion were constructed using the Erase-a-Base kit (Promega, Madison, Wis.). Double stranded sequencing of each deletion series was performed using the Sequenase Kit (US Biochemical, Cleveland, Ohio) or the T7 DNA Polymerase Sequencing Kit (Pharmacia, Milwaukee, Wis.). Sequences were aligned and analyzed using DNASIS sequence analysis software for IBM-compatible computers. Both strands of the genomic subclone were sequenced completely, but only one strand was sequenced to determine the location of the deletions in the BN115 promoter/GUS fusion series.

Figure 5:
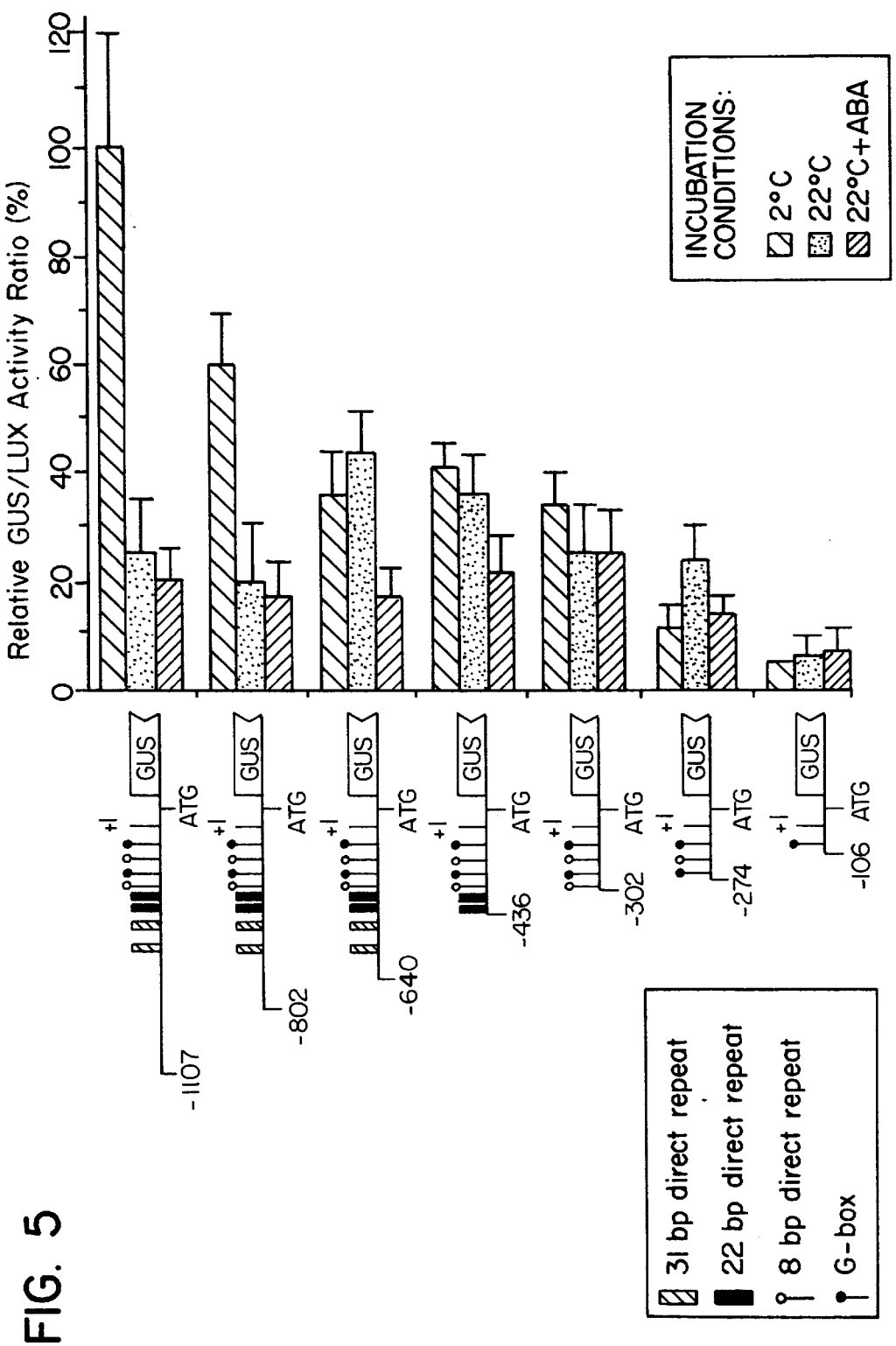
FIG. 5 shows the effects of 5'-deletions on the transient expression of GUS by the BN115 promoter. Linear maps of the inserts from the series of plasmids containing increasingly larger deletions from the 5' end of the BN115 promoter/GUS fusion in pUC119/115P-GUS are shown on the left. The stopping position of each deletion is shown along with remaining repeated elements. Histogram shows the relative GUS/luciferase (LUX) activity ratios measured in bombarded Jet neuf leaves after 24–48 h as described in the Examples. All activity ratios were normalized to that of the full-length promoter/GUS construct at 2° C. set at 100%. Values shown represent the mean (+S.E.) net GUS/net LUX activity (in nmol MU (methyl umbelliferone) produced $min^{-1}$ $mg^{-1}$/$mVsec^{-1}$$\mu g^{-1}$) determined for 4–6 independent experiments as described in the Examples.

Using fluorometric analyses of transient expression, the full-length BN115 promoter/GUS construct (bp −1107 to +100 of FIG. 2; 156 to 1362 of SEQ ID NO:1) was found to be approximately 5-fold more active in leaves that had been incubated for 24 or 48 h at 2° C. than in those incubated at 22° C. on the same media with or without ABA (FIG. 5). Fusion of BN115 sequences from bp −2200 to +100 (i.e. the whole cloned fragment) with the GUS reporter gene did not further increase the activity of the promoter in this transient expression system (data not shown).

Deletion of the 5'-distal 305 bp (from bp −1107 to −802 of FIG. 2; 156 to 461 of SEQ ID NO:1) results in a 40% decrease in the activity of the BNI115 promoter at 2° C. (FIG. 5) but has no effect on its activity at 22° C. (plus or minus ABA). Thus, the cold-inducibility of this promoter, as determined by fluorometric GUS activity normalized to LUX activity, has been reduced from 5- to 3-fold suggesting that this region may contain enhancer sequences. Deletion of the next 162 bp (to −640 of FIG. 2; 623 of SEQ ID NO:1) decreases promoter activity at 2° C. by an additional 25% (to about 35% of the full-length promoter activity). In addition, this deletion results in a 2-fold increase in the promoter activity at 22° C., but only in the absence of ABA (FIG. 5). Deletion of the next 204 base pairs (to −436 of FIG. 2; 827 of SEQ ID NO:1) has little effect on the promoter activity at either 2° C. or 22° C. (plus or minus ABA). Similarly, deletion of the region containing the 22 bp direct repeat (through (to bp −302 of FIG. 2; 961 of SEQ ID NO:1) causes little, if any, decrease in activity at either temperature. However, subsequent deletion analysis showed that this 302 bp promoter fragment is the smallest that can still support GUS expression in the cold at a level equivalent to or greater than that at 22° C. in bombarded Jet neuf leaves (FIG. 5).

Deletion to bp −274 (of FIG. 2; 989 of SEQ ID NO:1) causes a 2 to 3-fold decrease in the activity of the promoter at 2° C. from that of the previous deletion to −302 (of FIG. 2; 961 of SEQ ID NO:1) but does not affect the activity of the promoter at 22° C. (no ABA) (FIG. 5). Thus, with the removal of only 28 bp, cold activity drops to below that of room temperature and is virtually eliminated. Interestingly, this 28 bp fragment contains the first half of the 8 bp direct repeat (TGGCCGAC) that is present in the promoter of the A. thaliana BN115 homologue cor15 (Baker et al., 1994, Plant Mol Biol 24: 701–713) and which contains a consensus sequence CCGAC that is present in the 9 bp (TACCGACAT) dehydration response element (DRE) identified in the upstream region of the A. thaliana cold-, salt- and drought-induced gene rd29A (Yamaguchi-Shinozaki and Shinozaki, 1994, Plant Cell 6: 251–264). A 71 bp fragment of this gene containing the downstream 9 bp DRE was shown to be able to direct the production of GUS transcripts in transgenic A. thaliana in response to cold treatment. In addition, the 9 bp DRE was not present in the promoter of the rd29B gene, which is not cold-induced (Yamaguchi-Shinozaki and Shinozaki, 1994, Plant Cell 6: 251–264).

Subsequent deletion to bp −106 (of FIG. 2; 1157 of SEQ ID NO:1), which removes the region containing the second 8 bp LTRE (TGGCCGAC), results in significant loss of promoter activity (to less than 10% of that of the full-length promoter at 2° C.) under all conditions tested (FIG. 5). The remaining sequences, a single G-box and the putative TATA box, are therefore insufficient to maintain gene expression at a level equivalent to that of the full-length promoter at 22° C. (20–25% of the full-length promoter at 2° C.).

Figure 6:
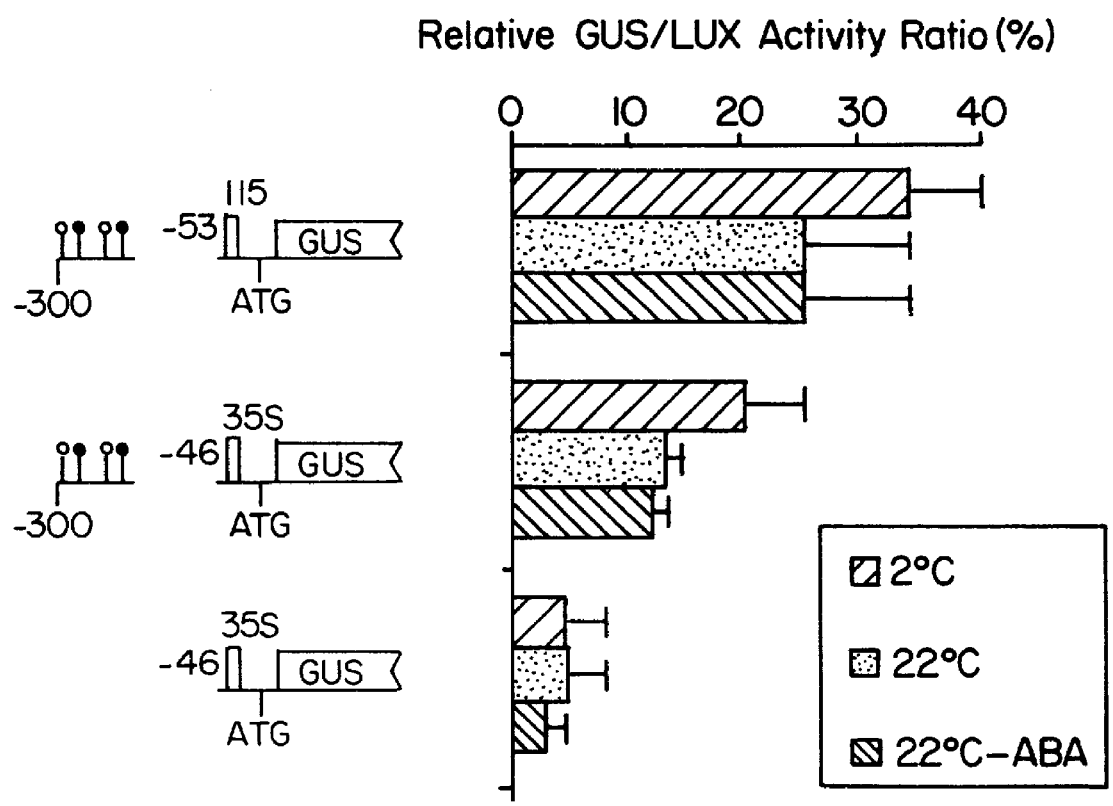
FIG. 6 shows the results of the test for the presence of cold-responsive elements in BN115 promoter sequences from −300 to −53 (of FIG. 2; 963 to 1210 of SEQ ID NO:1)

To verify that the region from bp −300 to −53 (of FIG. 2; 963 to 12 10 of SEQ ID NO:1) is able to direct low temperature GUS expression, this region was amplified by the polymerase chain reaction (Saiki et al., 1988, Science 239: 487) from 1 ng of pUC119/115P-GUS using the primers 5'-GGGTAGATCTACTAACATG-3' (upstream) and 5'-GGATTGCAGCTGGTCTAG-3' (downstream), generating BglII and PvuII sites at −300 (963 of SEQ ID NO: I) and −53 (1210 of SEQ ID NO:1), respectively. This fragment was inserted into the polylinker of pUC119 (Yanisch-Perron et al., 1985, Gene 33: 103–119) and sequenced. An error-free subclone was isolated and the "−300" fragment isolated by digestion with KpnI and SphI and the ends blunted with T4 DNA polymerase. BglII linkers were then ligated onto the ends of the blunted fragment and inserted into the unique BglII site upstream of the truncated CaMV 35S promoter in the plasmid pEMBL46GUS3C (Fang et al., 1989, Plant Cell 1: 141–150). Transient GUS expression from the resulting plasmid, −300/−46GUS, was monitored in microprojectile-bombarded Jet neuf leaves as described for the deletion series. As shown in FIG. 6, GUS expression from −300/−46GUS was 1.5-fold higher at 2° C. than at 22° C. The −302 deletion of the BN115 promoter/GUS fusion also showed a similar fold of cold induction although the absolute activities were higher with the BN115 deleted fragment (FIG. 6). In addition, GUS expression from −300/−46GUS' at 2° C. was about 5-fold higher than GUS expression from either pEMBL-46GUS3C or the −106 deletion (FIG. 5) at 2° C. suggesting that this fragment has the ability to direct low temperature gene expression.

Effect of ABA on Transient GUS Expression from BN115 Promoter Deletions in winter *B. napus* Leaves Within experimental error, no ABA-inducible GUS expression was detected in any of the extracts prepared from winter *B. napus* cv Jet neuf leaves that had been bombarded with the BN115 promoter/GUS fusion deletion plasmids (FIG. 5). Uptake of ABA by the leaves from the semi-solid media was confirmed by the detection, on Northern blots, of BN28 transcripts, which have been shown to be induced by cold and, to a lesser degree, by ABA (Orr et al., 1992a, Plant Physiol 98: 1532–1534) (results not shown). Total RNA was isolated from leaf tissue using a phenol-chloroform extraction procedure (Sambrook, et al., 1989, *Molecular Cloning. A Laboratoy Manual*, Second Edition. New York: Cold Spring Harbor Laboratory Press). For Northern blot analysis, 10 or 20 μg of total RNA was denatured, subjected to electrophoresis in formaldehyde/1.5% agarose gel and then transferred to Nytran (Schleicher and Schuell, Keene, N.H.) membranes (Sambrook et al., 1989, *Molecular Cloning: A Laboratory Manual*, Second Edition. New York: Cold Spring Harbor Laboratory Press). Filters were hybridized with a $^{32}$P-labelled ssDNA probe prepared using the Random Primers DNA Labeling System (Gibco/BRL, Gaithersburg, Md.) with the insert of pBN115 (Weretilnyk et al., 1993, Plant Physiol 101:171–177) or pBN28 (Orr et al., 1992a, Plant Physiol 98: 1532–1534) as template and following the manufacturer's protocol. However, no ABA-induced transcripts hybridizing to a BN115 probe were detected in the RNA isolated from these same leaves (results not shown). On the other hand, similar analysis of total RNA isolated from non-bombarded *A. thaliana* leaves that had been surface-sterilized and incubated on ABA-containing media for 6 h showed the accumulation of significant levels of BN115-hybridizing transcripts (FIG. 6c). These ABA-induced messages in *A. thaliana* most likely represent cor15 transcripts, which have previously been shown to accumulate in ABA-treated leaves (Hajela et al., 1990, Plant Physiol 93: 1246–1252). Thus, ABA uptake from the semi-solid media is sufficient to induce the expression of BN28 in winter *B. napus* leaves and cor15 in *A. thaliana* leaves, but not BN115 in winter *B. napus* leaves.

GUS Expression from BN115 Promoter Containing Mutations or Substitutions

FIG. 7 shows the linear maps of the BN115 promoter indicating mutations and replacement of specific domains within the promoter region. 7A shows the wild-type promoter. In 7B the first LTE region has been mutated from CCGAC to AATTC. FIG. 7C shows a similar mutation wherein the mutation occurs at the second LTRE region. In FIG. 7D, both LTRE regions, CCGAC were mutated to AATTC. The last construct shown, FIG. 7E, demonstrates the replacement of region −1155 to −605 (of FIG. 2; 108 to 658 of EQ ID NO:1) with an enhancer from the cauliflower mosaic virus 35S promoter.

The resulting expression of GUS at 2° C. and 22° C. is shown in FIG. 8. The mutation of a CCGAC sequence to AATTC in each or both of the repeat resulted in loss of cold induced transient expression after microprojectile bombardment with the constructs as described previously for FIG. 6. Furthermore, the replacement of the putative enhancer region of the promoter, with the enhancer from the cauliflower mosaic virus 35S promoter, resulted in several-fold increase in cold-induced gene expression. Thus, providing a stronger cold-inducible promoter.

All scientific publications and patent documents are incorporated herein by reference.

The present invention has been described with regard to preferred embodiments. However, it will be obvious to persons skilled in the art that a number of variations and modifications can be made without departing form the scope of the invention as described in the following claims.

We claim:

1. An isolated DNA molecule comprising a 5' regulatory region of a low temperature-responsive gene BN115 from *Brassica napus*, comprising nucleotides 961–1210 of SEQ ID NO:1.

2. The isolated DNA molecule according to claim 1 comprising nucleotides 961–1362 of SEQ ID NO:1.

3. The isolated DNA molecule of claim 2 comprising nucleotides 461–1362 of SEQ ID NO:1.

4. The isolated DNA molecule of claim 3 comprising nucleotides 156–1362 of SEQ ID NO:1.

5. The isolated DNA molecule of claim 4 comprising nucleotides 23–1271 of SEQ ID NO:1.

6. The isolated DNA molecule of claim 5 comprising nucleotides L- 1271 of SEQ ID NO:1.

7. An isolated cold inducible promoter, or a functional fragment thereof capable of regulating the expression of a gene in response to a change in temperature, said cold inducible promoter comprising nucleotides 1–1271 of SEQ ID NO:1.

8. An isolated DNA molecule comprising a sequence of at least 15 contiguous nucleotides of a 5' regulatory region of a low temperature responsive gene BN115 from *Brassica napus*, as defined by nucleotides 1–1271 of SEO ID NO:1.

9. The isolated promoter of claim 7, also comprising a heterologous enhancer region.

10. A vector comprising the isolated DNA molecule of claim 8.

11. A vector comprising the isolated promoter of claim 7.

12. A method of controlling the expression of a gene in response to changes in temperature comprising placing the gene within the vector of claim 11 in such a manner that temperature dependent expression of the gene is obtained.

13. An isolated enhancer, or a functional fragment thereof each capable of mediating the expression of a gene under the control of a promoter and said enhancer or fragment, said enhancer obtained from the regulatory region of BN115 from *Brassica napus*.

14. The isolated enhancer of claim 13 comprising nucleotides 156–461 of SEQ ID NO:1.

15. The isolated enhancer of claim 13 comprising nucleotides 156–623 of SEQ ID NO:1.

16. An isolated negative regulatory element capable of repressing gene expression at 22° C., obtained from the regulatory region of BN115 from *Brassica napus* and comprising nucleotides 461–623 of SEQ ID NO:1.

17. The isolated DNA molecule of claim 6 also comprising an enhancer.

18. The isolated DNA molecule of claim 6 also comprising an enhancer from the 35S cauliflower mosaic virus promoter.

* * * * *

UNITED STATES PATENT AND TRADEMARK OFFICE
CERTIFICATE OF CORRECTION

PATENT NO. : 5,847,102
DATED : December 8, 1998
INVENTOR(S) : Singh et al.

It is certified that error appears in the above-identified patent and that said Letters Patent is hereby corrected as shown below:

On the cover page, [73] should read:
Assignee: Her Majesty in right of Canada as represented by Agriculture and Agri-Food Canada, of Ottawa, Canada

Column 3, line 45, between ")" and "contain" insert --in the BN115 promoter is an A/T-rich region that appears to--

Column 6, line 16, "IS" should read "ID" and line 45, change "-705" to -- -605--

Col. 17, line 44, "SEO" should read "SEQ".

Signed and Sealed this

Sixth Day of July, 1999

Attest:

Q. TODD DICKINSON

*Attesting Officer*   Acting Commissioner of Patents and Trademarks

UNITED STATES PATENT AND TRADEMARK OFFICE
CERTIFICATE OF CORRECTION

PATENT NO. : 5,847,102
DATED : December 8, 1998
INVENTOR(S) : Singh et al.

It is certified that error appears in the above-identified patent and that said Letters Patent is hereby corrected as shown below:

Column 6, line 17, change "434" to "-434"

Column 12, line 51, change "12 10" to "1210"

Column 14, line 23, change "EQ" to "SEQ"

In Claim 6, line 2, change "L- 1271" to "1-1271"

Signed and Sealed this

Twenty-sixth Day of October, 1999

Attest:

Q. TODD DICKINSON

*Attesting Officer*       *Acting Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 2218
        ( B ) TYPE: Nucleic Acid
        ( C ) STRANDEDNESS: Double- Stranded
        ( D ) TOPOLOGY: Linear ( i i ) MOLECULE TYPE: Genomic DNA ( i i i ) HYPOTHETICAL: No ( i v ) ANTI-SENSE: No ( v ) FRAGMENT TYPE:

( v i ) ORIGINAL SOURCE:
        ( A ) ORGANISM: Bassica napus (vii) IMMEDIATE SOURCE:
  (A) LIBRARY:
  (B) CLONE: plasmid pUC119

(viii) POSITION IN GENOME:

(ix) FEATURE:

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (H) DOCUMENT NUMBER:
  (I) FILING DATE:
  (J) PUBLICATION DATE:
  (K) RELEVANT RESIDUES IN SEQ ID NO:

(xi) SEQUENCE DESCRIPTION: SEQ ID NO: 1:

```
TTAGAAAGTT  TAAAATTTAA  TACTTGAACA  TGTGAAAGAT  TTTTCTTTTA  AAATATGATT      60
TTAGAAAAAA  AATATATTAT  CTAATTTTA   TTTATTTTAT  TATTAAAAAC  TGACATGTCA     120
CTACATATAA  CATGTAAATG  AATAGTCATC  TTGCGGTCGA  CATTGAAAGA  TTCATGTTCT     180
AAGATTTAGT  TACAATTTGA  TGAACAAATA  AGTTAAGTTT  AAAGTTTTTT  GCGATACAAA     240
TGTTAGGTTG  AAAGTTTAAA  ATGCTAATGA  AAAACTTTAA  AAGTTTAAAG  TGTTAATGAA     300
TACCACTTTG  AGGGTTTTTA  TGCAATTTTA  TGCAATTTTC  TCAATTTTTA  AGTTACCCAT     360
CTAGGTACAA  AAATATTTTA  AACCATTTTG  TCCAAGATTC  GTGATTTCTT  TGAGCCGGTC     420
CTGATGGCTT  GGCTCTGATG  TACCAGAAAA  TCGATGCACC  ACGCTAATAT  TTTGTACAAA     480
AAAAAATCAA  TGTTATATAG  CATTCAATGA  AACGATTTAA  CCCATTTTGT  AAATCCTAAT     540
TGAAAAAACT  AATCTTGCAC  CCGGTGACCG  TTATATATGC  AACTTTGTGA  AAATATGGTT     600
TGTAGTTTTT  ATTTAAGCTA  TTACACCATG  TCTGTTTAGA  AGTTCCTAGT  GGATAGGATA     660
TCTCTGAAAG  TGACGTTAAT  TAATTGTTAT  TTATGTAATG  GTATGCCTTT  TAAAATTACA     720
AAAATTGGTT  TTAGTAGATA  AATATGTTGT  TTAAAGGAAA  ATAAATATAA  TGGTATGCCT     780
TTTGAAATTA  CAAATATGAC  GTTAATTAAT  TGTTATTTAT  GTAATGGAAC  CCCATGAAAT     840
ACCATAAACC  ATATATCACT  CTATAAGTGT  GATAGGCTTG  CCATCATATA  CGTTATATTT     900
TTATATCTAT  ATTTTGAAAA  CTTTTTAGGC  TTGCCATCAT  ATACGTTTTT  TTTTTTTGGG     960
GTAGATTTAC  TAACATGTTG  GCCGACGTAT  ACTTTTGTTT  TTATCACAAC  AAAGGTGGTA    1020
CACGTGAAGT  AACGATAACG  ACCCACAACT  CCGATTTCTT  TGTGTTTAAT  TTTGCAAAAA    1080
ATAAAAGCAG  AAATGCTAAC  ATGTATATCA  CCACAAGTTT  TGATGGCCGA  CCTGTTTTTT    1140
CAATAGTTAA  AGAAAATAAC  ATCAATGCAT  TATAAAAAAA  TTCTACGATG  CCACGTGATT    1200
TGGATTGCAG  TTGGTCTAGT  ATCTATAAAA  CTATGATACT  ATTGGAGAAT  AGATTATTAC    1260
TCATCTCACT  CTTGTTCCTA  TTAAAACTCC  TCCTTTGATT  TCTTTTGCTC  GCTTTTGACT    1320
CTTTAAAGAG  AACTTTC ATG GCT ATG TCA CTC TCA GGA TCA GCT GTT CTC            1370
ATT GGG ATT GGT TCT TCT TTC TCC AGC GGC ATA GCC AAG CAG AGC GGC           1418
GTT GGC GCC GTC GGT TTT GGC CGG AAA ACT GAG CTC GTC GTC GTC GCT           1466
CAG CGC AAG AAG TCG TTG ATC TAC GCC GAT AAA GGT GAC GGC AAC ATT           1514
CTG GAT GAC CTC AAT GAA GCC ACG TAAGTCTAAT CTTATTCACC CAAAAACTCT          1568
CATATATATA  TATATTATTA  CTAACCATGA  TATTACAATA  TCATTCAAGA  TATAGAGGTT    1628
CATAAACCAT  AATATATAAT  TGATATCTCT  TCTAATTTTT  TAGTTTACAT  ATTGACTCAA    1688
```

-continued

| | | | | | |
|---|---|---|---|---|---|
| ATATTTGAAA | ATTAAGTAAG | ATACTTCCAT | GTTAGCCAAT | GTGGATATAC | GTTTTGTCAA | 1748
| CAATGAATCT | GAATATACAC | ATACATGAAC AGA AAG AGA GCT TCG GAT TAC GCG | | | | 1802
| ACG GAG AAG ACA AAG GAG GCG TTG AAA AAT GGC GAG AAA GCA AAA GAC | | | | | | 1850
| TAC GTT GTT GAT AAG AAC GTT GAA GCC AAA GAC ACT GCA GTG GAT GAA | | | | | | 1898
| GCT CAG AAA GCT TTG GAT TAT GTG AAG GCA AAA GGA AAC GAA GCT GGG | | | | | | 1946
| AAC AAA GTT GCC GAG TTT GTT GAG GGT AAA GCA GGA GAG GCT AAG GAC | | | | | | 1994
| GCC ACA AAA GCA TGATGCTTCA ACCACTTAAC TCTAGATATA TATATATATC | | | | | | 2046
| TAGATTATCC | TTGTTGTCTC | ATGTTTATTA | TTTTACAATA | AGATCAGTTT | GTTTAAAACT | 2106
| TCTATTTCAC | TAGTTGAAAT | AAAGATATGT | TACTTAACTA | CTCATCATTA | TATCTTGATG | 2166
| ATGTCTTCAA | AGTATATCAA | TGAGAAACTT | AATAAAAGAG | AACTTTTATG | GA | 2218